(12) United States Patent
Kobayashi

(10) Patent No.: US 6,378,375 B1
(45) Date of Patent: Apr. 30, 2002

(54) METHOD FOR NON-DESTRUCTIVE DETECTION FOR FOREIGN MATTER IN MEDIUM USING WAVEFORM OF ULTRASONIC WAVE

(75) Inventor: Wataru Kobayashi, Tokyo (JP)

(73) Assignees: OpenHeart Ltd., Tokyo; A Limited Responsibility Company, Research Network, Kyoto, both of (JP)

( * ) Notice: Subject to any disclaimer, the term of this patent is extended or adjusted under 35 U.S.C. 154(b) by 0 days.

(21) Appl. No.: 09/413,501

(22) Filed: Oct. 6, 1999

(30) Foreign Application Priority Data

Oct. 7, 1998 (JP) ............................................ 10-300415

(51) Int. Cl.⁷ ............................................. G01N 29/16
(52) U.S. Cl. ......................................................... 73/600
(58) Field of Search .................... 73/596, 597, 598, 73/599, 600, 602, 606, 609, 627, 628, 629

(56) References Cited

U.S. PATENT DOCUMENTS

| | | | | |
|---|---|---|---|---|
| 5,092,176 A | * | 3/1992 | Buttram et al. ............... | 73/599 |
| 5,243,862 A | * | 9/1993 | Latimer ........................ | 73/600 |
| 5,359,898 A | * | 11/1994 | Latimer ........................ | 73/600 |
| 5,433,203 A | * | 7/1995 | Kimura et al. .......... | 128/660.06 |
| 5,559,292 A | * | 9/1996 | Hull et al. ..................... | 73/597 |
| 5,629,485 A | * | 5/1997 | Rose et al. .................... | 73/599 |
| 5,824,908 A | * | 10/1998 | Schindel et al. .............. | 73/632 |
| 5,900,935 A | * | 5/1999 | Kelin et al. .................. | 356/347 |
| 5,932,806 A | * | 8/1999 | Rose et al. .................... | 73/599 |
| 5,955,669 A | * | 9/1999 | Egami .......................... | 73/579 |

* cited by examiner

Primary Examiner—Richard A. Moller
(74) Attorney, Agent, or Firm—Duane Morris LLP

(57) ABSTRACT

This invention intends to provide a method for inspecting an inner state of an object by determining whether or not any foreign matter is generated inside the object material without being affected by any outside state of the object. This method comprises irradiating waveform of ultrasonic wave to an object whose inner state is desired to be inspected from outside, extracting waveform of a reflected wave traveling inside the object, detecting a difference of acoustic impedance of the foreign matter from the waveform of the reflected wave by extracting a deflection of the waveform and detecting for presence/absence of the foreign matter inside the object or presence/absence of the foreign matter and a quantity of the foreign matter.

4 Claims, 6 Drawing Sheets

ORIGINAL WAVEFORM OF SCATTERED ULTRASONIC WAVE OF TEST PIECE (A)

RELATION BETWEEN ω AND τ UPON REFLECTION

METHOD FOR NON-DESTRUCTIVE DETECTION FOR FOREIGN MATTER IN MEDIUM USING WAVEFORM OF ULTRASONIC WAVE

BACKGROUND OF THE INVENTION

1. Field of the Invention

This application discloses using ultrasonic testing (UT) as a non-destructive testing (NDT) method for detecting impurities contained in a metal.

2. Description of the Related Art

The prior art generally does not consider non-destructive methods for determining the amount of impurities absorbed by and present in a particular piece of metal. Particularly, UT has never been used to detect impurities in metal because the metal oxide formed on the exterior of the metal interferes with ultrasonic absorption and scattering in the metallic sample. Additionally, for the particular case of hard to detect impurities such as hydrogen, the hydrogen atoms are too small to be detected by conventional UT.

Hydrogen impurities are of particular concern in metal. Hydrogen embrittlement is a common problem in metal: a metal, immersed in water during normal use, absorbs some hydrogen atoms that are present in the water. Absorbing these hydrogen impurities makes the metal brittle, shortening the useful life of the metal. It would be helpful to know whether or not, and to what extent, metal used in an aqueous environment has absorbed hydrogen atoms. More generally, it would be useful to be able to determine the presence and concentration of impurities present in any metal.

3. Summary of the Invention

The present application discloses using UT to determine the concentration of impurities in a metal, notwithstanding the presence of an oxide layer on the surface of the metal under test. This method comprises the steps of: (a) directing a test ultrasonic wave towards the metal under test; (b) measuring as a function of time the amplitudes of the reflected waves reflected from the test metal; (c) detecting a phase deflection in the reflected waves from the reflections caused by an impurity; and (d) relating this phase deflection to the presence and concentration of an impurity in the test metal.

DESCRIPTION OF THE PREFERRED EMBODIMENTS

When a sound wave traveling in a homogenous medium encounters an impurity, the sound wave will reflect off of that impurity if the difference in acoustic impedance between the medium and the impurity is sufficiently large. This impurity-reflected wave is also deflected in phase relative to a reflected wave that does not encounter an impurity before reflecting. Determining the concentration of the impurities in the metal by observing this difference in phase deflections is the basic premise underlying applicant's disclosure.

This difference in reflected wave form deflections however is small, and thus the difference is difficult to observe. Therefore in applicant's disclosure, an extremely short interval is used to analyze the deflection of the waveform. Generally, an ultrasonic wave is generated by an ultrasonic generator and is directed towards a test piece. The ultrasonic wave is reflected by the outer surface of the test piece, the bottom surface of the test piece and any impurities in the test piece. The waves reflected from the test piece are detected, and the amplitudes of the reflected sound waves are determined as a function of time. Additionally noise may be detected as well which may distorted the detected waves. By filtering the reflected waves, only those waves that are reflected by the impurities are analyzed to determine the presence and concentration of the impurities in the test piece.

Figure 1:
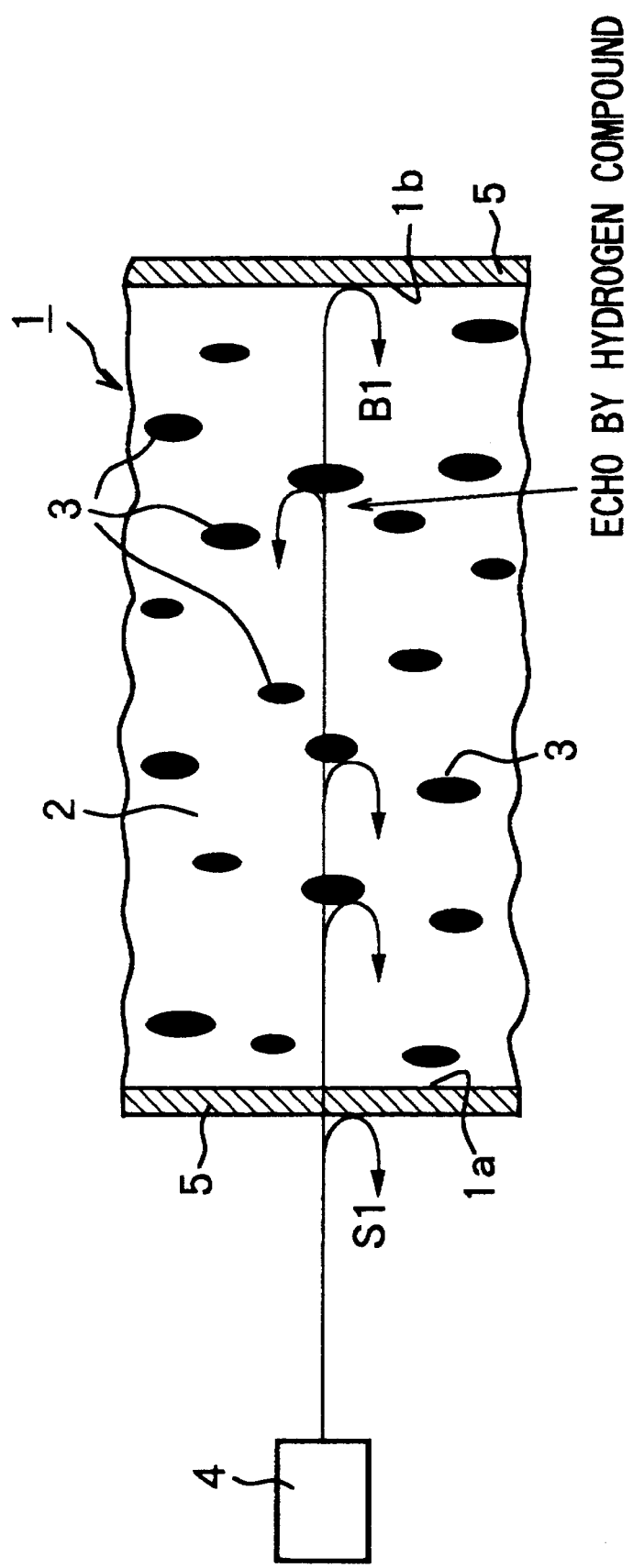
FIG. 1 is a schematic view of a section of an alloy wall of a test piece containing hydrogen showing the reflected ray paths .

With Reference to FIG. 1, one embodiment of applicant's disclosure is illustrated. Ultrasonic waves from ultrasonic generator 4 are directed towards a metal 2 which is contaminated by randomly-located impurities. In the present embodiment the impurities are hydrogen impurities 3. Some of the ultrasonic waves S1 are reflected off of the outer surface 1a. The remaining ultrasonic waves pass into the metal 2. Once in the metal, some ultrasonic waves are reflected by the hydrogen impurities 3 and some pass through the metal 2 and then are reflected B1 by the bottom surface 1b. In the present embodiment only the waves that are reflected by the impurities are used to determine the concentration of the impurity and waves reflected off the outer surface S1 and bottom surface B1 are filtered out.

Figure 2:
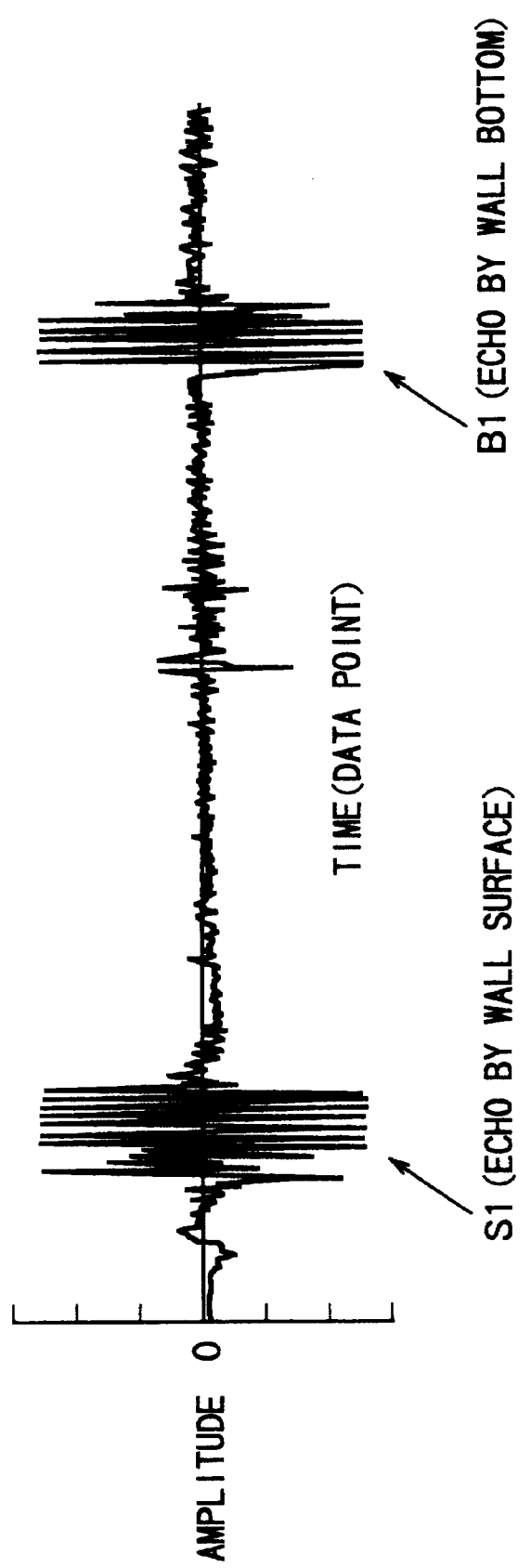
FIG. 2 is a reflected wave form diagram showing a reflected high frequency ultrasonic wave generated in a section of the test piece of FIG. 1.

As shown in FIG. 2, the S1 represents the reflection wave from the oxide film 5 of the outer surface 1a. B1 represents the reflection wave from the bottom surface 1b. The reflection wave situated between S1 and B1 represents the reflection form the hydrogen impurity.

Figure 3:
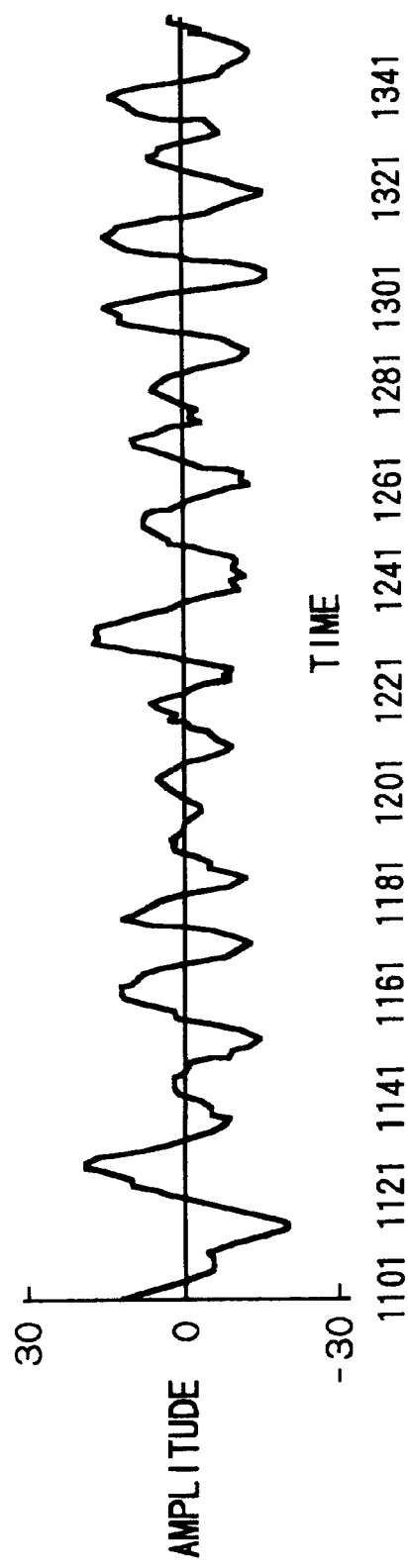
FIG. 3 is a reflected wave form diagram showing a reflected high frequency ultrasonic wave generated in a test piece A containing some hydrogen.

With reference to FIG. 3, a reflected wave form from test piece A having hydrogen impurities is illustrated as an amplitude over time graph. The "zero-cross" point represents a point at which the reflection component form the hydrogen impurity intersects the x-axis (either in the positive direction or the negative direction). By measuring the distance between two adjacent zero-cross points, the degree of flucuation corresponding to the adjacent zero-cross points can be measured. As illustrated in FIG. 3, a plurality of zero-cross points can be measured for a given test piece and thus the distance between two adjacent zero-cross points can vary. Therefore, the standard deviation of the distances between zero-cross points for a given test piece can be determined.

In one embodiment of the applicant's invention, a filter is used to precisely determine the degree of fluctuation corresponding to adjacent zero-cross pints. By employing a single FIR (Finite Impulse Response) filter having the characteristics of a band-pass filter or employing a direct connection between two FIR filters (a low-pass and a high-pass filter), only the components of the frequency band of a narrow range, i.e., those corresponding to the reflected waves form the impurities, are extracted, and the unnecessary reflected waves are excluded.

The measurement of the fluctuation of the zero-cross points are carried out according to the following steps:

the reflected waves form the impurity are filtered as described above;

measuring, for each adjacent pair of zero-cross points, the distance between the zero-cross points; and calculating the standard deviation of the fluctuation of the distance between the zero-cross points. The calculated standard deviation indicates the degree of fluctuation and can be correlated to determine the amount of impurity in the metal.

Figure 4:
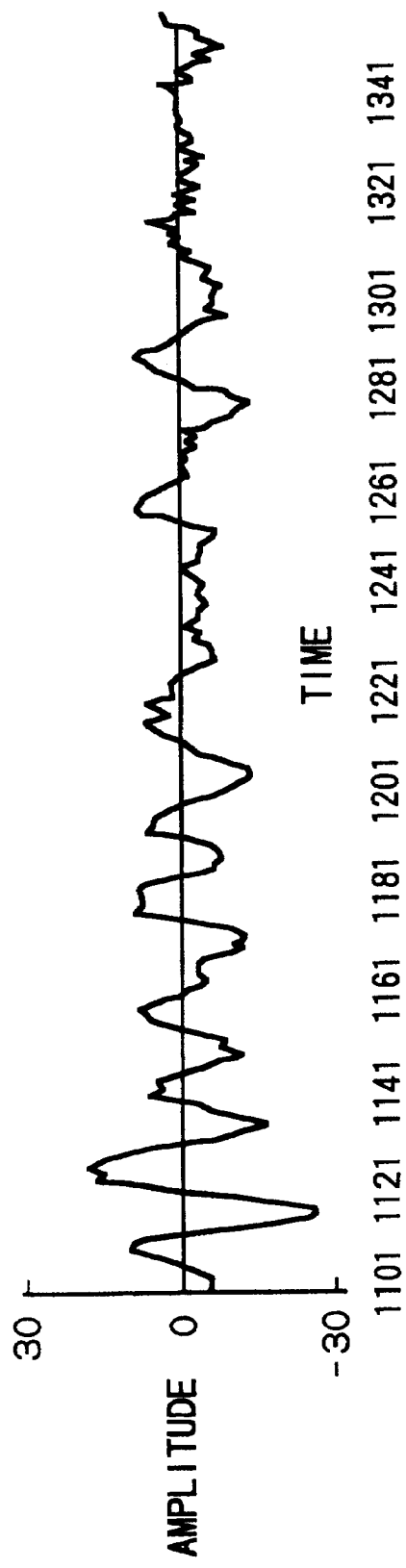
FIG. 4 is a reflected wave form diagram showing a reflected high frequency ultrasonic wave generated in a test piece B containing a greater amount of hydrogen than test piece A of FIG. 3.

The more impurity in the test material, the larger the phase fluctuations become. For example, FIG. 4 illustrates the reflected waves form from test piece B, where test piece B has more hydrogen impurities than test piece A. Note that the distance between adjacent zero-cross points associated with test piece B in FIG. 4 are greater than the distances associated with the zero-cross points associated with test piece A of FIG. 3.

The method of the present invention can be further explained by examining a change of particle density due to sound pressure of ultrasonic waves traveling in a medium. This examination is described below.

Figure 5:
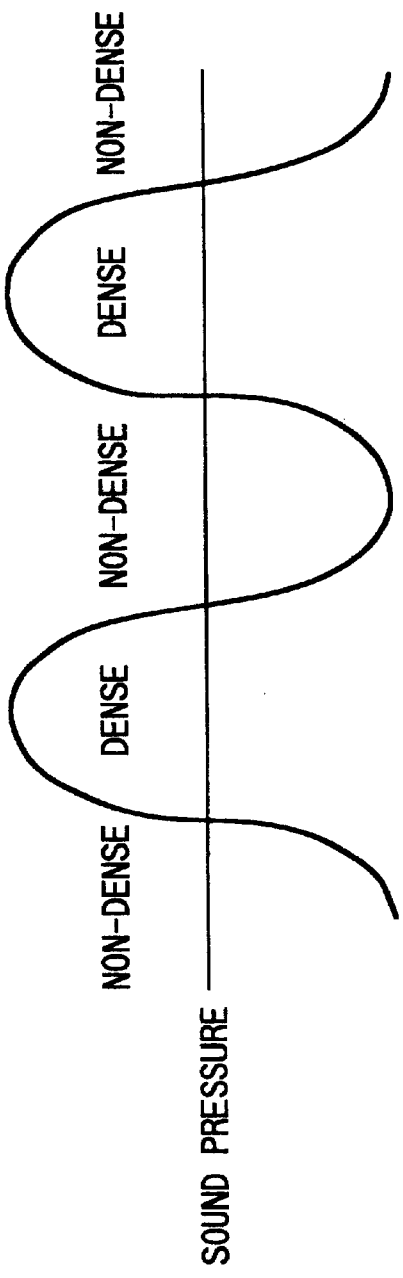
FIG. 5 shows a relation between the particle density of an object and sound pressure.

When sound wave travels in a medium, a change of density occurs in that medium as shown schematically in FIG. 5. That is, a change of the density is repeated with a cycle of sound wave such that the density of the medium is intensified in a portion having a high sound pressure and the density thereof becomes weak at a portion having a low sound pressure. Now, assuming that the density of a medium is $\rho$, a mass of a unit area $\Delta x$ as a minute portion of medium perpendicular to $\chi$ direction which is a traveling direction of sound wave is $\rho \cdot \Delta x$.

Next if the aforementioned $\rho \cdot \Delta x$ is substituted for mass m of Newton's equation of motion, $F = ma = m \cdot d^2x/dt^2$, $$F = m \cdot a = m \cdot \partial^2 u/\partial t^2 = (\rho \cdot \Delta x) \cdot \partial^2 u/\partial t^2 = P \cdot \partial^2 u(x) = \partial x^2 \cdot \Delta x$$

where u is an amount of deflection of medium and P is static pressure in the medium If both sides of the aforementioned expression is divided by $\Delta x$, $\rho \cdot \partial^2 u/\partial t^2 = \partial^2 u/\partial x^2$. If $P/\rho = c$ is placed, $\partial^2 u/\partial t^2 = \partial^2 u/\partial x^2$.

Where c is sound velocity and this expression is first-order wave equation.

Next if the above wave equation is solved using angular frequency $\omega = 2\pi f$, a general solution shown in Expression 1 is obtained.

$$u(x,t) = Ae^{-j(kx-\omega t)} + Be^{j(kx+\omega t)} \qquad \text{[Expression 1]}$$

where $k = 2\pi\lambda$, $\lambda$ is wave length of sound wave and A, B are arbitrary constants.

Because $E = \rho v$ when a particle velocity of medium is assumed to be v, sound-pressure E of the sound wave can be obtained if the particle velocity v is determined. Because a general solution of the aforementioned wave equation expresses a deflection (distance) of the medium, the particle velocity of the medium can be introduced by differentiating this equation by t.

Therefore, the sound pressure E of the sound wave is expressed as shown in Expression 2.

$$E = \rho \cdot v = \rho \cdot du/dt = j\omega\rho\{Ae^{-j(kx-\omega t)} + Be^{j(kx+\omega t)}\} \qquad \text{[Expression 2]}$$

The first term of this expression expresses progressive wave and the second term expresses regressive wave.

If the medium is uniform, its change occurs relatively evenly and therefore it does not appear as a conceivable observation result. If there are incontinuous points in the medium, it is assumed that reflection does not occur at the incontinuous points and there occurs a difference in the observation result depending on the frequency of reflections.

Considering an influence by the inertia of the particle upon reflection, an apparent velocity of a particle colliding with the incontinuous point in the medium drops due to spring constant (Young's modulus of elasticity) of the medium when the direction of its force is changed by the reflection.

Figure 6:
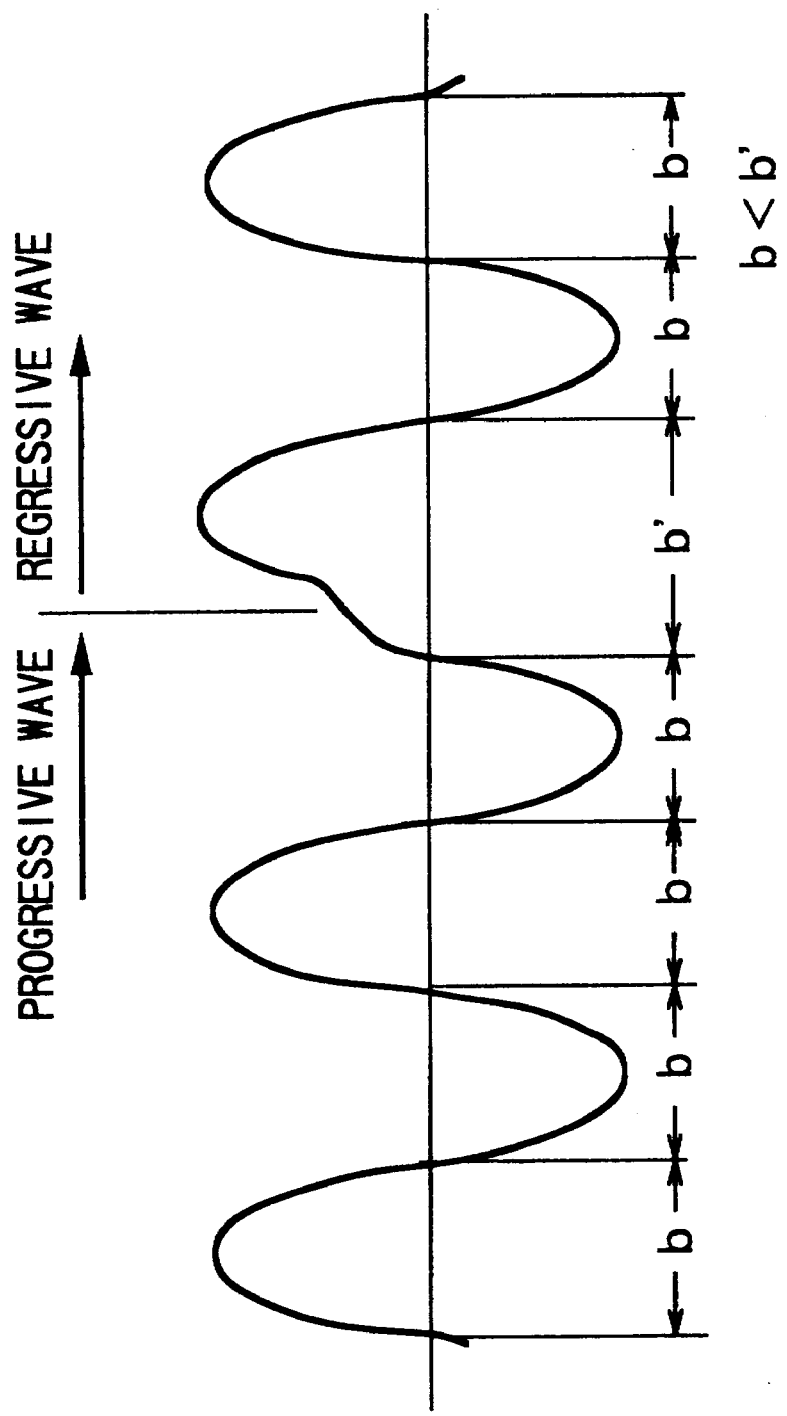
FIG. 6 is a wave form diagram showing a phase deflection obtained according to the present invention.

Therefore, when the sound wave is reflected, $\omega$ is retarded relative to t. FIG. 6 shows a change of the sound pressure by an influence of the spring constant upon reflection.

Although such an ideal waveform is not seen in actual waveform because of multiple reflections, an entire tendency of the waveform can be grasped with this Figure.

Because the Expression 3 is obtained if this is applied to the aforementioned expression, it is made evident that when the sound wave is reflected, apparently the frequency is lowered. Thus, as the irregular reflection increases, the number of reflected waves whose frequency is deflected increases.

$$E = j\omega\rho\{Ae^{-j(kx-(\omega-n)t)} + Be^{j(kx+(\omega+n)t)}\} \qquad \text{[Expression 3]}$$

However, this transient phenomenon upon reflection vanishes within a single cycle. Therefore, upon observation, it is necessary to see not a change of the frequency characteristic due to Fourier transformation but a tendency of a deflection of the phase of each cycle. Thus, the detection method of the present invention is effective.

As described above, the present invention comprises: irradiating waveform of ultrasonic wave to an object whose inner state is desired to be inspected from outside; extracting waveform of a reflected wave traveling inside the object; detecting a difference of acoustic impedance of the foreign matter—from the waveform of the reflected wave by extracting a deflection of the waveform; and detecting for presence/absence of the foreign matter inside the object or presence/absence of the foreign matter and a quantity of the foreign matter. As a result, a foreign matter generated in a homogeneous medium, which cannot be found by a conventional non-destructive detection method using ultrasonic wave, can be detected accurately even if it is minute or the quantity thereof is small.

What is claimed is:

1. A method for non-destructive detection for foreign matter in medium using waveform of ultrasonic wave, comprising:

irradiating waveform of ultrasonic wave to an object whose inner state is desired to be inspected from outside;

extracting waveform of a reflected wave traveling inside the object;

detecting a difference of acoustic impedance of the foreign matter from the waveform of the reflected wave by extracting a deflection of the waveform; and detecting for presence/absence of the foreign matter inside the object or presence/absence of the foreign matter and a quantity of the foreign matter.

2. A method for non-destructive detection for foreign matter in medium using waveform of ultrasonic wave according to claim 1 wherein the waveform of the reflected wave is processed via a processing portion composed of mainly a waveform filter, a feature of the deflection of the phase of the waveform is extracted from the waveform processed in said processing portion and a degree of the deflection and a quantity of the foreign matter in the medium are quantified.

3. A method for non-destructive detection for foreign matter in medium using waveform of ultrasonic wave according to claim 2 wherein for the feature and degree of the deflection of the phase, an interval of zero crossing points of the reflected wave is extracted so as to convert a standard deviation thereof to numeric value and a quantity of the foreign matter in the medium and a size of the foreign matter is quantified based on said numeric value.

4. A method for non-destructive detection for foreign matter in medium using waveform of ultrasonic wave according to claim 1–3 wherein a waveform of ultrasonic wave to be irradiated is high-frequency ultrasonic wave.

\* \* \* \* \*